US00PP09437P

United States Patent [19]

Zaiger et al.

[11] Patent Number: Plant 9,437

[45] Date of Patent: Jan. 23, 1996

[54] NECTARINE TREE 'LIZ'S LATE'

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 365,353

[22] Filed: Dec. 12, 1994

[51] Int. Cl.[6] ..... A01H 5/00

[52] U.S. Cl. ..... Plt./41.3

[58] Field of Search ..... Plt./41.3

[56] References Cited

PUBLICATIONS

Fogle, H. W., et al. (Listing for) "'Lizzie'" *North American and European Fruit and Tree Nut Germplasm Resources Inventory* 1981 USDA Misc. Pub. #1406, p. 304.

*Primary Examiner*—James R. Feyrer

[57] ABSTRACT

The present new and distinct variety of nectarine tree has the following unique combination of desirable features that are outstanding in a new variety:

1. Fruit with an attractive red skin color.
2. Late maturity of freestone fruit.
3. Fruit with good flavor and eating quality.
4. Fruit with firm flesh, good storage and shipping quality.
5. Heavy and regular bearing of fruit.
6. Relatively uniform size fruit throughout the tree.

1 Drawing Sheet

ORIGIN OF THE VARIETY

The present variety of nectarine tree was originated by us in our experimental orchard located near Modesto, Calif., from a second generation seedling of a cross between two selected seedlings with the field identification numbers 60G329 and 20G902. The maternal parent 60G329 originated from a second generation seedling of a cross between Sun Grand Nectarine (U.S. Plant Pat. No. 974) and Merrill Gem Peach (U.S. Plant Pat. No. 868). The pollen parent 20G902 originated from a cross between a nectarine of unknown parentage and Autumn Grand nectarine (U.S. Plant Pat. No. 2,894). A large group of these second generation seedlings were planted and grown under careful and continual observation by us, during which time we recognized the desirable fruit characteristics described above and selected the present variety for asexual reproduction and commercialization.

ASEXUAL REPRODUCTION OF THE VARIETY

Asexual reproduction of the new and distinct variety of nectarine tree by budding was performed by us in our experimental orchard located near Modesto, Calif., and shows that all characteristics of the tree and its fruit run true to form and are established and transmitted in succeeding propagations.

SUMMARY OF THE VARIETY

The new and distinct variety of nectarine tree is of large size, vigorous, upright in growth and is productive and regular bearer of large, yellow flesh freestone fruit with good flavor and eating quality. The fruit is further characterized by having firm flesh with good storage and shipping ability, being relatively uniform in size throughout the tree and in comparison to the clingstone Nectarine August Glo (U.S. Plant Pat. No. 8,039) which ripens in the same maturity season, the fruit of the new variety is freestone.

PHOTOGRAPH OF THE NEW VARIETY

The accompanying photograph shows a reproduction in color of typical specimens of the foliage and fruit of the present variety. It depicts the upper and lower surface of the leaves, an exterior and sectional view of the fruit, with a fruit being divided on its suture plane to reveal flesh coloration and to show a stone remaining in place. The photographic illustration was taken shortly after the fruit was picked (firm ripe) and the colors are as nearly true as is reasonably possible in a color representation of this type.

DESCRIPTION OF THE VARIETY

The following is a detailed botanical description of the new nectarine tree, its flowers, foliage and fruit, based on observations of specimens grown near Modesto, Calif., with color terminology (except those in common terms) referenced to Reinhold Color Atlas by A. Kornerup and J. H. Wansher.

Tree:
- *Size.*—Large.
- *Vigor.*—Vigorous.
- *Density.*—Medium dense.
- *Form.*—Upright.
- *Productivity.*—Productive.
- *Bearing.*—Regular.

Trunk:
- *Size.*—Large.
- *Texture.*—Medium shaggy.
- *Color.*—Hair brown to brown (5-E-4) to (5-F-4).

Branches:
- *Size.*—Medium.
- *Texture.*—Medium rough.
- *Lenticels.*—Medium number. Medium size.
- *Color.*—Camel brown to sunburn brown (6-D-4) to (6-D-5).

Leaves:
- *Size.*—Large. Average length — 7½". Average width — 1⅞".
- *Texture.*—Smooth.
- *Margin.*—Crenate.

*Petiole.*—Medium length. Medium thickness.

*Glands.*—Reniform. Number varies from 0 to 4. Average number 2. Medium size. Located on the upper portion of the petiole and the lower portion of the leaf blade.

*Form.*—Lanceolate.

*Color.*—Upper surface — green to dark green (29-D-5) to (29-F-5). Lower surface — grayish green to green (29-D-7) to (29-E-7).

Flower buds:

*Size.*—Medium to large.

*Form.*—Plump.

*Length.*—Medium.

Flowers:

*Size.*—Large — showy.

*Blooming period.*—Mar. 3, 1993 to Mar. 9, 1993. Varies slightly with climatic conditions.

*Pollen.*—Present. Self fertile.

*Color.*—Pink.

Fruit:

*Maturity when described.*—Firm ripe.

*Date of first picking.*—Aug. 13, 1993.

*Date of last picking.*—Aug. 18, 1993.

*Size.*—Large. Average diameter axially — 2⅞". Average transversely in suture plane 2⅝".

*Form.*—Nearly globose, slightly elongated, flattened at base.

*Suture.*—Shallow, extends from base to apex.

*Ventral surface.*—Very shallow, varies from slight depression to nearly round.

*Cavity.*—Rounded to slightly elongated in suture plane. Average depth ½". Average breadth 15/16".

*Base.*—Retuse.

*Apex.*—Varies from rounded to slight pistol point.

Skin:

*Thickness.*—Medium.

*Texture.*—Medium — Tenacious to flesh.

*Tendency to crack.*— *None.*

*Down.*—Wanting.

*Color.*—Ground color — Golden yellow to light orange (5-A-5) to (5-A-7). Overspread with orange red to red (9-A-7) to (9-B-8).

Flesh:

*Texture.*—Firm.

*Ripens.*—Evenly.

*Juice.*—Moderate.

*Flavor.*—Mild, good balance between acid and sugar.

*Fibers.*—Few, small, tender.

*Eating quality.*—Good.

*Aroma.*—Moderate.

*Amygdalin.*—Undetected.

*Color.*—Light yellow to maize yellow (4-A-4) to (4-A-6). Pit cavity — red to deep red (10-B-7) to (10-C-8). Red bleeds into flesh around pit cavity. Small white flecks of callus formed between flesh fibers and stone.

Stone:

*Type.*—Freestone.

*Size.*—Medium to large. Average length — 1⅜". Average width — 1". Average thickness — ½".

*Base.*—Mostly rounded — Varies from straight to rounded.

*Apex.*—Acuminate.

*Form.*—Oval — elliptic.

*Sides.*—Mostly equal — varies from equal to unequal.

*Surface.*—Irregularly furrowed toward apex with the longest furrows near the outer edges. Pitted toward the base.

*Ridges.*—Rounded.

*Tendency to split.*—Very slight.

*Color.*—Reddish brown to brown (9-E-5) to (9-E-7). Small white flecks of callus adhering to stone surface.

Use: Dessert.

*Market.*—Local and long distance.

Keeping quality: Good.

Shipping quality: Good.

The new nectarine tree, its flowers, foliage and fruit, herein described may vary in slight detail due to climate, soil conditions and cultural practices under which the variety may be grown; the present description is that of the variety grown under the ecological conditions prevailing near Modesto, Calif.

We claim:

1. A new and distinct variety of nectarine tree, substantially as illustrated and described, which is of large size, vigorous, upright in growth and a productive and regular bearer of large, firm, yellow flesh, freestone fruit with good flavor and eating quality; the fruit is further characterized by being nearly uniform in size throughout the tree, having good storage and shipping quality and, in comparison to August Glo Nectarine (U.S. Plant Pat. No. 8,039), the new variety matures in the same maturity season but is freestone instead of clingstone.

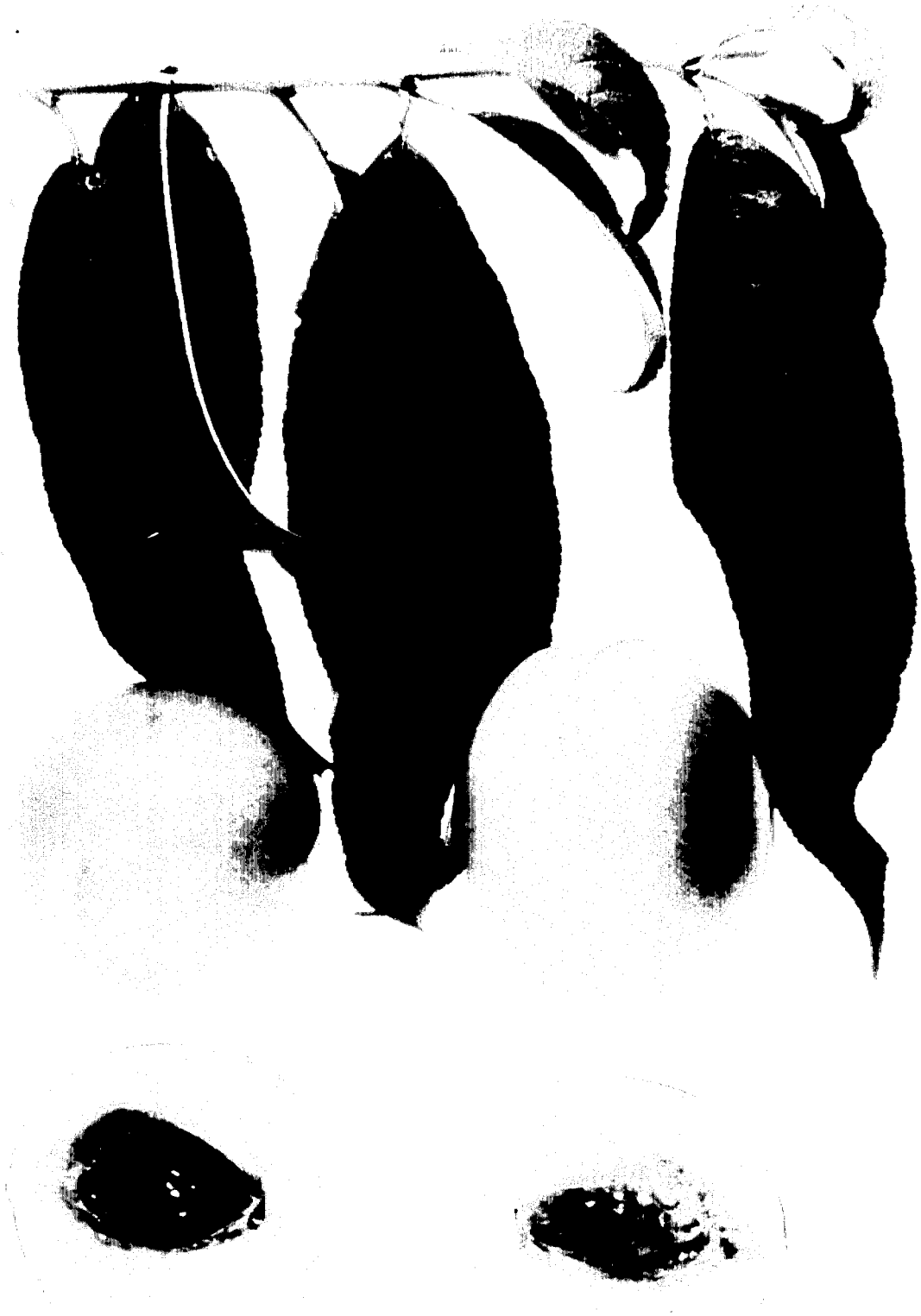

* * * * *